United States Patent

Gerdau et al.

Patent Number: 5,231,224
Date of Patent: Jul. 27, 1993

[54] ALKYL ETHER CARBOXYLIC ACID TAURIDES

[75] Inventors: Thomas Gerdau, Eppstein; Alwin Reng, Kelkheim; Walter Kunz, Hattersheim am Main, all of Fed. Rep. of Germany

[73] Assignee: Hoechst Aktiengesellschaft, Frankfurt am Main, Fed. Rep. of Germany

[21] Appl. No.: 833,999

[22] Filed: Feb. 11, 1992

[30] Foreign Application Priority Data

Feb. 12, 1991 [DE] Fed. Rep. of Germany ....... 4104226

[51] Int. Cl.$^5$ .............................................. C07C 61/00
[52] U.S. Cl. ................................... 562/105; 562/107; 252/121; 252/117; 424/70
[58] Field of Search ................ 562/105; 252/121, 117; 424/70

[56] References Cited

U.S. PATENT DOCUMENTS 3,232,968 2/1966 Schenck et al.

FOREIGN PATENT DOCUMENTS 1197885 8/1965 Fed. Rep. of Germany .
3412094 10/1985 Fed. Rep. of Germany .
411221 4/1966 Switzerland .
0783038 7/1957 United Kingdom ................ 562/105
930929 7/1963 United Kingdom .
934379 8/1963 United Kingdom .

OTHER PUBLICATIONS

Chem. Abs. 114:61539B (1991), abstract of JP 02-218657.
Derwent Abstract of JP 02-218657 Aug. 31, 1990.

*Primary Examiner*—Jose G. Dees
*Assistant Examiner*—Keith MacMillan

[57] ABSTRACT

The invention relates to alkyl ether carboxylic acid taurides of the formula $$R^2-(OC_2H_4)_n-O-CH_2-CO-NR^1-C_2H_4-SO_3M,$$

in which n is greater than 0, $R^1 = H$ or $C_1-C_4$ alkyl, $R^2 = C_5-C_{22}$ alkyl and $M = H$, Na, K, Ca/2 or Mg/2.

Processes for their preparation and their use as surface-active substances, especially as mild cleaning agents for cosmetic purposes, are also described.

9 Claims, No Drawings

ALKYL ETHER CARBOXYLIC ACID TAURIDES

DESCRIPTION

The invention relates to alkyl ether carboxylic acid taurides, to their preparation and to their use. Cosmetic and technical cleaning agents are conventionally prepared with anionic, cationic, amphoteric and non-ionic surface-active substances, which are used, on their own or in the form of combinations within these groups, as active substances. The primary task of these preparations, for example in the case of cosmetic cleaning preparations, is the specific removal of endogenous and exogenous dirt on the skin, hair and teeth. Because of the modern tendency to wash one's hair and shower every day, it is becoming more and more desirable to have surfactants with a mild, i.e. weak cleaning action and at the same time a good compatibility with the skin and ocular mucosa.

The majority of commercially available surfactants, such as soaps, alkylsulfates, alkyl ether sulfates, alkylbenzenesulfonates and alkanesulfonates, only satisfy these requirements to a limited extent. Attempts are therefore being made to improve the application properties by using special surfactants on their own or by mixing them with the afore-mentioned classes of surfactants.

A known class of surfactants with outstanding properties are the fatty acid N-methyltaurides. They are characterized by a very good foaming power in soft water, a good dispersive power towards lime soaps and an acceptable compatibility with the skin. Nevertheless, these fatty acid N-methyltaurides do not satisfy the demands on high-quality surfactants in all applications. Thus, for example, the foam stability in hard water is often inadequate.

Other disadvantages are the difficult regulation of consistency, i.e. the lack of ability to thicken in aqueous solution, both on their own and in combination with other anionic surfactants such as e.g. alkylsulfates or alkyl ether sulfates, and the mediocre compatibility with the ocular mucosa, which plays a significant role when these surfactants are used in hair shampoos, for example.

It has now been found that taurides of alkyl ether carboxylic acids of formula I:

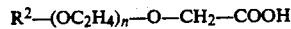

do not have these disadvantageous properties.

The invention therefore relates to alkyl ether carboxylic acid taurides of formula II:

in which n is greater than 0, preferably 1 to 12 and especially 2 to 6, $R^1$=H or $C_1$-$C_4$ alkyl, $R^2$=$C_5$-$C_{22}$ and especially $C_{10}$-$C_{22}$ alkyl and M=H, Na, K, Ca/2 or Mg/2. These compounds are surface-active substances and can advantageously be used wherever it is desirable or necessary to lower the surface tension of water. This applies for example to use in the preparation of cosmetic and technical cleaning agents such as hair shampoos, shower products, bath preparations, toothpastes, hand washing-up liquids, fire extinguishing foams, car shampoos and fabric detergents, but in particular in preparations which come into short-term or long-term contact with human skin when used.

Preferred surfactants are especially the N-methyltaurides of alkyl ether carboxylic acids, i.e. $R^1$=methyl.

The compounds of the invention are used especially in the form of their sodium, potassium, calcium or magnesium salts.

The properties of the alkyl ether carboxylic acid taurides can be varied within wide limits by the choice of the alkyl radical $R^2$ and the degree of ethoxylation n and can be matched to the requirements of the particular application. The compounds according to the invention are usually in the form of mixtures having different alkyl radicals $R^2$ and different degrees of ethoxylation n. $R^2$ includes linear and branched alkyl radicals; the carbon atom of the alkyl radical $R^2$ linked to the oxygen atom is a primary or secondary carbon atom.

Suitable starting materials for the preparation of the compounds according to the invention ar alkyl ether carboxylic acids of formula I which are also commercially available, such as e.g. ®Akypo RLM (manufactured by Chem-Y), ®Marlowet 4543 (manufactured by Hüls) or ®Sandopan D-LW (manufactured by Sandoz). Another possibility is to use special alkyl ether carboxylic acids which are accessible either from fatty alcohol ethoxylates and sodium chloroacetate or by the catalytic oxidation of fatty alcohol ethoxylates. Under certain circumstances, it may be desirable to use alkyl ether carboxylic acids which have been prepared from fatty alcohol ethoxylates with a narrow homolog distribution. Fatty alcohol ethoxylates with a narrow homolog distribution are obtained by reacting fatty alcohols with ethylene oxide in the presence of antimony pentahalides as catalysts (British patent 796,508; U.S. Pat. No. 3,359,331).

The subsequent preparation of the compounds according to the invention is carried out by reacting the alkyl ether carboxylic acids with thionyl chloride, phosphorus trichloride, phosgene or the like to give the corresponding acid chlorides, which in turn are reacted with aqueous tauride solutions by the conventional procedure under Schotten-Baumann conditions.

The products according to the invention are valuable anionic surface-active substances with many uses. Thus, for example, they are used as wetting agents, foaming agents or detergents. They can be used as aqueous solutions or as dry powders. In the latter case, the water is removed for example by distillation or drying.

If, for particular applications, the product has to be substantially salt-free, the salt is removed in a manner known per se, e.g. by reverse osmosis.

Where necessary, the surfactants according to the invention are used in diverse ways in combination with known anionic, non-ionic, cationic and/or amphoteric surfactants, it being possible for the amounts of alkyl ether carboxylic acid taurides combined with the particular classes of surfactants to be greater or less than the stoichiometric amounts.

The invention is illustrated in greater detail by the following Examples:

EXAMPLE 1

The starting material used was a coconut fatty alcohol which was ethoxylated with 2 mol of ethylene oxide in conventional manner with antimony pentachloride as catalyst (narrow homolog distribution) and oxidized to coconut alkyl glycol ether carboxylic acid on a platinum catalyst according to European patent document A-0 206 054. 144.5 g (0.5 mol) of the acid prepared in this way were heated to 60° C. with 1 ml of dimethylformamide, and 77.5 g (0.65 mol) of thionyl chloride were added over one hour. When the evolution of gas had ended, stirring was continued for a further hour at 60° C. and low-boiling constituents were removed under a water-jet vacuum to give 155 g of coconut alkyl glycol ether carboxylic acid chloride. The resulting acid chloride was added dropwise over two hours to a mixture of 220 g of 37% sodium N-methyltauride solution and 250 g of water. The pH was kept in the range between 9 and 10 by the simultaneous addition of sodium hydroxide solution. When the reaction was complete, stirring was continued for a further hour and the pH was adjusted to 7 with hydrochloric acid to give 695 g of an aqueous solution of the sodium salt of coconut alkyl glycol ether carboxylic acid N-methyltauride. The content of washing-active substance was 25.1% by Epton's method. The critical micelle concentration (CMC) is 0.26 g/l.

EXAMPLE 2

A solution of the sodium salt of coconut alkyl diglycol ether carboxylic acid N-methyltauride was prepared analogously. The content of washing-active substance was 24.7%. The critical micelle concentration is 0.19 g/l.

EXAMPLE 3

A solution of the sodium salt of $C_{12}$–$C_{15}$ alkyl triglycol ether carboxylic acid N-methyltauride was similarly prepared on the basis of a mixture of synthetic alcohols having $C_{12}$–$C_{15}$ alkyl groups. The content of washing-active substance was 24.3% by Epton's method. The critical micelle concentration is 0.12 g/l.

The following Application Examples show the broad range of possible uses of the alkyl ether carboxylic acid taurides in cleaning agents for cosmetic applications, for the household and for technical purposes. Unless mentioned otherwise, the amounts and percentages in the Examples are by weight in each case.

EXAMPLE 4

Hair shampoo

| | |
|---|---|
| Alkyl ether carboxylic acid tauride prepared according to Example 1 | 60.00% |
| Lauryl alcohol + 3 mol of ethylene oxide | 3.00% |
| Perfume oil | 0.30% |
| Sodium chloride | 0.30% |
| Water | ad 100.00% |

EXAMPLE 5

Foam bath

| | |
|---|---|
| Alkyl ether carboxylic acid tauride prepared according to Example 3 | 68.00% |
| Lauryl alcohol + 3 mol of ethylene oxide | 3.00% |
| Perfume oil | 0.50% |
| Water | ad 100.00% |

EXAMPLE 6

Shampoo for everyday use

| | |
|---|---|
| Alkyl ether carboxylic acid tauride | 50.00% |
| prepared according to Example 1 | |
| Lauryl alcohol + 3 mol of ethylene oxide | 3.00% |
| Magnesium acylamido diglycol ether sulfate | 8.00% |
| Sodium chloride | 1.50% |
| Water | ad 100.00% |

EXAMPLE 7

Shampoo for dry hair

| | |
|---|---|
| Alkyl ether carboxylic acid tauride prepared according to Example 2 | 57.00% |
| Polyethylene glycol 6000 distearate | 3.20% |
| Water | ad 100.00% |

EXAMPLE 8

Antidandruff shampoo

| | |
|---|---|
| Alkyl ether carboxylic acid tauride prepared according to Example 1 | 18.00% |
| Sodium lauryl diglycol ether sulfate (28%) | 38.00% |
| Sodium chloride | 2.00% |
| Antidandruff ingredient ® Octopirox (Hoechst AG) | 0.75% |
| Water | ad 100.00% |

EXAMPLE 9

Antidandruff shampoo

| | |
|---|---|
| Alkyl ether carboxylic acid tauride prepared according to Example 3 | 20.00% |
| Sodium lauryl triglycol ether sulfate (28%) | 40.00% |
| Sodium chloride | 1.80% |
| Antidandruff ingredient ® Octopirox (Hoechst AG) | 0.50% |
| Water | ad 100.00% |

EXAMPLE 10

Shower product

| | |
|---|---|
| Alkyl ether carboxylic acid tauride prepared according to Example 1 | 18.00% |
| Sodium laurylsulfate (34%) | 30.00% |
| Coconut fatty acid diethanolamide | 3.00% |
| Water | ad 100.00% |

EXAMPLE 11

Shower product

| | |
|---|---|
| Alkyl ether carboxylic acid tauride prepared according to Example 3 | 20.00% |
| Triethanolamine laurylsulfate (40%) | 25.00% |
| Coconut fatty acid diethanolamide | 3.00% |
| Perfume oil | 0.50% |
| Water | ad 100.00% |

EXAMPLE 12

Liquid hand cleaner

| | |
|---|---|
| Alkyl ether carboxylic acid tauride prepared according to Example 1 | 12.00% |

| -continued | |
|---|---|
| Sodium alkyl diglycol ether sulfate (28%) | 32.00% |
| Sodium secondary alkanesulfonate (60%) | 5.00% |
| Coconut fatty acid diethanolamide | 3.00% |
| Sodium chloride | 0.90% |
| Water | ad 100.00% |

EXAMPLE 13

Baby shampoo

| | |
|---|---|
| Alkyl ether carboxylic acid methyltauride prepared according to Example 3 | 45.00% |
| Protein fatty acid condensation product, average molecular weight 500 | 3.00% |
| Coconut amphocarboxyglycinate | 5.00% |
| Lauryl alcohol + 3 mol of ethylene oxide | 3.00% |
| Sodium chloride | 2.00% |
| Water | ad 100.00% |

The afore-mentioned Application Examples show the possible uses of the alkyl ether carboxylic acid methyltaurides in cosmetic cleaning agents. Naturally, cleaning agents for the household, washing-up liquids, detergents, protective pastes, syndet soaps and the various cleaning agents for technical application sectors can also be prepared in similar manner.

The additives conventionally employed in practice, such as dyes, pearlescent agents, perfume oils, active ingredients, antioxidants, chelating agents, preservatives and the like, can also be used in known manner in the cleaning preparations.

In the following experiments, various properties of the alkyl ether carboxylic acid taurides prepared according to Examples 1, 2 and 3 are compared with those of commercially available anionic surfactants.

1 Foaming power

The foaming power was determined in water of 0° and 20° dH at a temperature of 43° C. by the ROSS-MILES method (F. J. Gohlke: Die Bestimmung des Schaumvermögens von Detergentien nach "ROSS-MILES" (The determination of the foaming power of detergents by the "ROSS-MILES" method), Parfümerie und Kosmetik 45, 359–363, 1964). The sodium salt of coconut fatty acid methyltauride (commercial product) was used as the comparative substance. The foam height is given in each case in mm; WAS means washing-active substance.

| % WAS | Alkyl ether carboxylic acid methyltauride according to | | | | | | Sodium salt of coconut fatty acid methyltauride | |
|---|---|---|---|---|---|---|---|---|
| | Example 1 | | Example 2 | | Example 3 | | | |
| | 0° dH | 20° dH | 0° dH | 20° dH | 0° dH | 20° dH | 0° dH | 20° dH |
| 1.0 | 230 | 240 | 230 | 240 | 240 | 240 | 220 | 210 |
| 0.1 | 220 | 220 | 210 | 210 | 220 | 220 | 210 | 200 |
| 0.03 | 200 | 200 | 190 | 190 | 200 | 200 | 170 | 170 |
| 0.006 | 130 | 130 | 130 | 120 | 130 | 120 | 100 | 60 |
| 0.002 | 90 | 50 | 80 | 40 | 60 | 50 | 40 | 35 |

The values show that, as regards foam stability, the surfactants according to the invention are markedly superior to the commercially available comparative product.

2. Consistency-imparting properties

The consistency-imparting properties of surfactants play an important role especially in their practical use for the manufacture of medium-viscosity to high-viscosity thickening preparations.

To test this behavior, a mixture containing 10% of WAS, composed of 7% of sodium lauryl diglycol ether sulfate and 3% of test product, is prepared. Sodium chloride is added to this mixture in increasing concentration and the resulting viscosity is measured with a Brookfield RV3 viscometer.

The values obtained in mPas for this mixture with alkyl ether carboxylic acid methyltaurides prepared according to Examples 1, 2 and 3 are recorded in the following Table.

| NaCl % | Alkyl ether carboxylic acid methyltauride according to | | |
|---|---|---|---|
| | Example 1 | Example 2 | Example 3 |
| | (3 parts by weight with 7 parts by weight of lauryl diglycol ether sulfate) | | |
| 7.0 | 42,400 | 32,300 | 38,200 |
| 8.0 | 55,200 | 38,600 | 34,300 |
| 9.0 | 30,550 | 21,000 | 27,000 |

The above values illustrate the favorable application behavior of the surfactants according to the invention with regard to their consistency-imparting properties.

3. Zein test

The zein test (see A. K. Reng et al., Erfahrungen mit Invitro-Methoden zur Charakterisierung kosmetischer Tenside (Experiences with in vitro methods of characterizing cosmetic surfactants), Parfümerie und Kosmetik 68, 771–778, 1987) gives preliminary information on the compatibility of surfactants with the skin.

High zein values, i.e. above 500 mg of nitrogen/100 ml, indicate strongly solubilizing surfactants with an unfavorable dermatological behavior. Zein values below 200, on the other hand, are a preliminary indication of so-called mild surfactants.

The surfactants according to the invention have the following values (zein values in mg of nitrogen/100 ml):

| | Alkyl ether carboxylic acid methyltauride according to | | | Sodium laurylsulfate |
|---|---|---|---|---|
| | Example 1 | Example 2 | Example 3 | |
| Zein value | 169 | 205 | 172 | 834 |

The above results show that the class of compounds is below the limit of 200 mg of nitrogen/100 ml and can thus be regarded as mild. The comparative substance sodium laurylsulfate had a zein value of 834 and is thus to be classified as a strong irritant.

4. Denaturation of hemoglobin

The denaturation of hemoglobin (according to Pape and Hoppe, Proceedings 2nd World Tenside Congress 1988, vol. 4) provides information on the behavior of surfactants on human skin. Due to complexation of the surfactant with globin, its structure changes and the color change of the hemoglobin can be measured by spectrophotometry. Sodium laurylsulfate is defined as having a denaturation index of 100%. The substances according to the invention had denaturation indices of between 40 and 50% and can thus be regarded as having a good compatibility.

What is claimed is:

1. An alkyl ether carboxylic acid tauride of the formula $$R^2-(OC_2H_4)_n-O-CH_2-CO-NR^1-C_2H_4-SO_3M,$$

in which n is greater than 0, $R^1$=H or $C_1$-$C_4$ alkyl, $R^2$=$C_5$-$C_{22}$ alkyl, and M=H, Na, K, Ca/2 or Mg/2.

2. A compound as claimed in claim 1, wherein, in said formula, n is 1 to 12.

3. A compound as claimed in claim 1, wherein, in said formula, $R^1$ is $C_1$-$C_4$ alkyl.

4. A compound as claimed in claim 3, wherein $R^1$ is methyl.

5. A compound as claimed in claim 1, wherein, in said formula, $R^2$ is $C_{10}$-$C_{22}$ alkyl.

6. A compound as claimed in claim 1, wherein, in said formula, n is 1 to 12, $R^1$ is methyl, and $R^2$ is $C_{10}$-$C_{22}$ alkyl.

7. A cleaning agent comprising a compound as claimed in claim 1 in combination with at least one of the following additives or active ingredients: a dye, a pearlescent agent, a perfume oil, an antioxidant, a chelating agent, a preservative, or an additional surfactant.

8. A cleaning agent as claimed in claim 7, wherein the active ingredient combined with the compound of claim 1 is a non-ionic, cationic, amphoteric, or second anionic surfactant, or a combination of said surfactants.

9. A cleaning agent for cosmetic, household, or industrial applications, containing at least one compound of claim 1.

* * * * *